United States Patent [19]

Moore

[11] Patent Number: Plant 5,331

[45] Date of Patent: Nov. 13, 1984

[54] MINIATURE ROSE PLANT

[75] Inventor: Ralph S. Moore, Visalia, Calif.

[73] Assignee: Sequoia Nursery, Visalia, Calif.

[21] Appl. No.: 458,145

[22] Filed: Mar. 14, 1983

[51] Int. Cl.[3] ..... A01H 5/00

[52] U.S. Cl. ..... Plt./10

[58] Field of Search ..... Plt./10

*Primary Examiner*—Robert E. Bagwill

[57] ABSTRACT

This invention relates to a new and distinct variety of miniature rose plant primarily identified by the unusual red color, the petals being dark red (near black red) on outside surface and a lighter red on inside surface.

1 Drawing Figure

1

The present invention relates to a new and distinct variety of hardy, dwarf, bush type rose plant of the miniature class; the variety being primarily characterized — as to novelty — by the very dark, near black, red of the outside surface of petals and the contrasting lighter red of inside surface and the Hybrid Tea form of buds and flowers.

The variety is further characterized by:

An abundance of bloom, with flowers usually borne singly, but also several to the stem in loose clusters.

Little or no fragrance.

A plant which is vigorous, of rounded, upright shape with small semi-glossy to matt foliage with pointed leaflets; the buds and flowers being similar in form and size to Fiesta Ruby (miniature — U.S. Plant Pat. No. 4,368).

The plant, which has a normal height of 12–14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Ca., under conditions of careful control and observation, as a cross between Baccara (U.S. Plant Pat. No. 1,367, expired — Hybrid Tea) as the seed parent and Little Chief (miniature — not patented) as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; upright; seedling; greenhouse; outdoors; cut flowers; garden decoration; potted plant.

Class: Miniature. Variety identification: MORblack: (Commercial synonym: Don Marshall).

Flowers borne: Singly and several together (3 to 5) on slender wirey stems.

2

Quantity of bloom: Abundant both outside and in greenhouse. Bud:

*Peduncle.*—Medium to long; slender but sturdy; erect; medium green, sometimes tinted bronze (outdoors); with no prickles and few or no short hairs.

*Before calyx breaks.*—Size — small. Form long; pointed with several foliaceous appendages on surface of bud; with foliaceous parts extending beyond the tip of the bud equal to one-half or less of its length. Color — medium to dark green, occasionally tinted with bronze (outdoors).

*As calyx breaks.*—Color — red.

*Opening.*—Opens well in all weather.

Bloom:

*Size when fully open.*—Small, averaging about 35 mm (1½").

*Petalage.*—Double — averaging about 60–70 petals arranged regularly plus several small petaloids.

*Form.*—High centered with petals rolled loosely outward and downward. Open flowers usually show no stamens.

Petals: Fairly thick; satiny on inside and on outside surface.

*Shape.*—Outside petals, broad lanceolate (nearly round), without acute tip; intermediate — broad lanceolate sometimes with acute tip; inside — lanceolate sometimes with acute tip.

Color: (Newly opened flower from a plant grown in plastic greenhouse (November 1982), Visalia, Calif.):

*Outside petal.*—Outside surface — sometimes as dark as Maroon 1030 or 1030/1 — more often near Crimson 834 becoming near Cardinal Red 822/1 on tip portion and with small near white area at base. Inside surface — near Currant Red 821/1 with darker area near base and small near-white area at base.

*Intermediate petal.*—Outside surface similar to outside petal. Inside surface similar to outside petal.

*Inner petal.*—Outside surface — same as intermediate petal; inside surface — same as intermediate petal. General color effect; buds and newly opened flowers — dark red. Three days open — color dark red. Behavior — opens well in all weather. Old flowers sometimes tend to "blue". Spent petals drop off. Flower longevity (September 1982) — plant in pot 4–6 days or longer. Cut flowers at living room temperature 4–6 days or longer.

Reproductive Organs:

*Stamens.*—Few or none.

*Filaments.*—Few or none, varying length, medium long.

*Anthers.*—Usually none.

*Pollen.*—None.

*Pistils.*—Average number.

*Styles.*—Varying length; greenish; bunched (not well formed).

*Ovaries.*—All enclosed in calyx.

*Hips.*—None.

*Sepals.*—Permanent; spear shaped; recurved.

*Seed.*—None.

Foliage:

*Leaves.*—Compound of five (sometimes three or seven) leaflets; medium small; leathery; semi-glossy to matt.

*Leaflets.*—Shape: broad, nearly oval; apex acute; base rounded — sometimes acute.

*Color.*—Medium green; new growth — normal (medium) green (sometimes tinted reddish).

*Rachis.*—Medium strength; upper side may have several tiny short hairs; grooved; underside may have several thorns (1-3).

*Stipules.*—Medium to short length; medium width; medium length narrow points which turn out usually at about 45 degrees or more.

Growth:

*Habit.*—Dwarf; bushy; upright; much branched.

*Growth.*—Free; vigorous; internodes short.

*Canes.*—Medium; slender; sturdy.

*Main stems.*—Color: medium green. Thorns: average. Prickles — none. Haris — none.

*Branches.*—Color: medium green. Thorns: average; slender; prickles: none. Hairs — none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, upright, much branched habit, substantially as illustrated and described, characterized by buds and flowers of exhibition form, essentially dark red in color, the petals on outside surface being darker (blackish) red than the red on inside surface, and further characterized by a plant of compact well rounded shape; vigorous, with the main stems and shoots being of average thorniness, the said plant being easy to propagate from cuttings or by budding, with an abundance of small semi-glossy to matt foliage and an abundance of flowers borne singly or several to the stem in loose clusters.

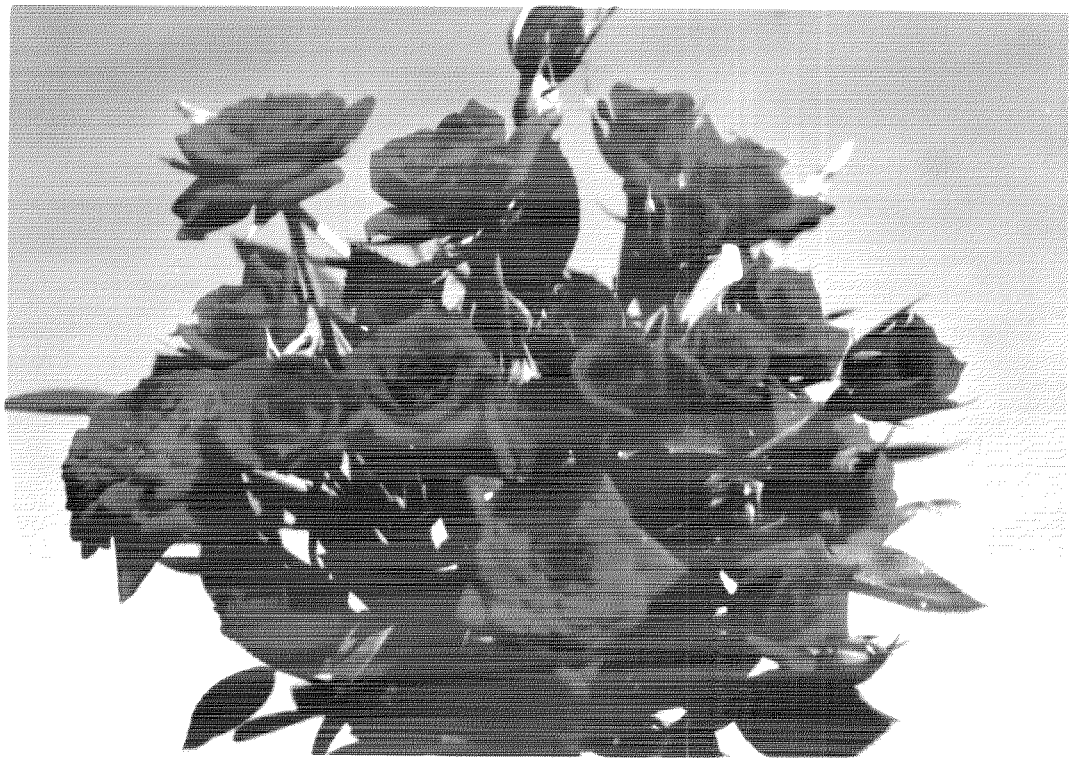

* * * * *